United States Patent [19]
Pozzi

[11] Patent Number: 5,975,894
[45] Date of Patent: Nov. 2, 1999

[54] EXPANSION SCREW FOR ORTHODONTICS

[75] Inventor: Alessandro Pozzi, Florence, Italy

[73] Assignee: Leone S.P.A., Sesto Fiorentino, Italy

[21] Appl. No.: 09/037,265

[22] Filed: Mar. 9, 1998

[30] Foreign Application Priority Data

Apr. 2, 1997 [IT] Italy ................................. FI97A0065

[51] Int. Cl.⁶ ..................................................... A61C 3/00
[52] U.S. Cl. ............................................................ 433/7
[58] Field of Search ........................................... 433/7, 18

[56] References Cited

U.S. PATENT DOCUMENTS

| 4,107,843 | 8/1978 | Spino et al. ................................ | 433/7 |
| 4,917,601 | 4/1990 | Williams ..................................... | 433/7 |
| 5,472,344 | 12/1995 | Binder et al. ............................... | 433/7 |

FOREIGN PATENT DOCUMENTS 1163244  4/1987  Italy .
641139   8/1950  United Kingdom .

*Primary Examiner*—John J. Wilson
*Attorney, Agent, or Firm*—McGlew AND Tuttle, P.C.

[57] ABSTRACT

Expansion screw for orthodontic plates or prothesis of synthetic resin, comprising at least one spindle (1) with at least a threaded portion (10), a block (3; 17) with through hole (31) for housing one part of the threaded portion (10) of spindle (1), guide means (2; 16) for moving each block (3; 17), means (11, 12) for actuating each spindle (1), wherein said hole (31) provided in each of said bodies (3; 17) has an inner diameter greater than the outer diameter of the corresponding threaded portion (10) of spindle (1) to allow for the interposition of a corresponding amount of resin in which a surface is cast of specular shape with respect to that of said threading and which takes up the form of the corresponding nut screw: each block (3) being integral with a corresponding element of the orthodontic plate or prothesis.

12 Claims, 5 Drawing Sheets

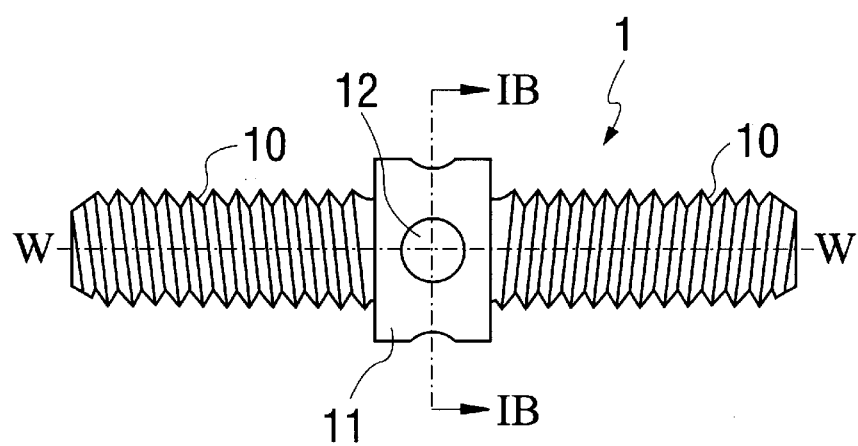
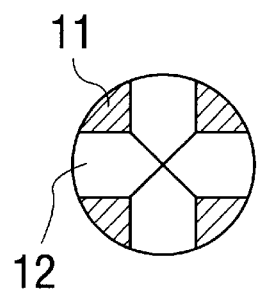
Fig. 1A
Fig. 1B
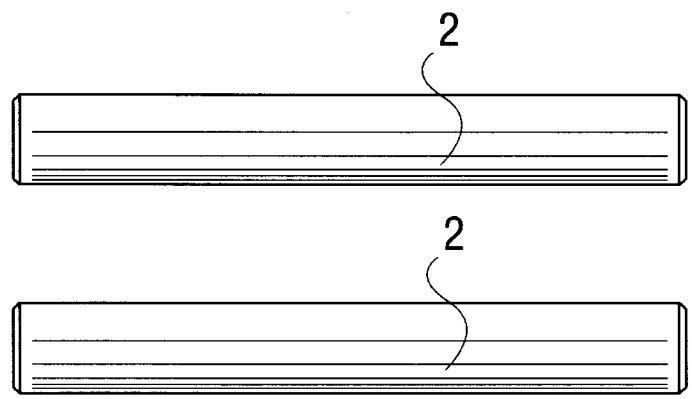
Fig. 1C

EXPANSION SCREW FOR ORTHODONTICS

FIELD OF THE INVENTION

The present invention refers to a screw for orthodontics, particularly of the type used in the construction of orthodontic prothesis or plates in synthetic resin.

BACKGROUND OF THE INVENTION

It is known to those skilled in the art that a bidirectional expansion screw for orthodontics comprises a central spindle, provided with counter-rotating threads on the two sides, and with a central, so-called "actuating" portion of larger diameter allowing the same spindle to be rotated by means of a pin-like tool able to be inserted into suitable recesses or holes formed on the surface thereof, said spindle being usually associated to two cylindrical and parallel rods connected to each other by metal blocks having longitudinal holes into which the same rods are positioned therethrough so as to form a guide assembly for driving the blocks together with the corresponding separate portions of an orthodontic plate or prothesis, as described later on. Formed in each of the blocks which connect said guide rods, is a threaded hole able to receive a corresponding side of the central spindle—as schematically illustrated in FIG. 1E of the attached drawings wherein the letter F indicates the threading and B the block in its whole—so that the rotation of the same spindle will determine the straight displacement of the blocks in opposite directions. Since each block is embedded into a corresponding element of the orthodontic plate, the movement of the blocks brings about the corresponding movement of the two plate elements and, therefore, in order to move these elements close to or away from each other, it is sufficient to turn the spindle by means of the suitable tool.

Based on the same principle is the operation of unidirectional, three-dimensional and fan-like openable expansion screws.

Expansion screws for orthodontics are also known from IT 1163244, U.S. Pat. No. 5,472,344 and GB 641139 documents.

One drawback in the manufacturing of orthodontic expansion screws of the type above described, lies in the fact that, to ensure the necessary stability and functionality of the screw connection between the central spindle and each block of the guide assembly, the construction accuracy is crucial, a factor which weighs heavily on the manufacturing costs because of the qualified labour and precision machines that must be relied on. Moreover, when assembling the various parts of the screw, it is necessary to screw every threaded side or shank of the central spindle into the female screw of the corresponding block of the guide assembly, which brings about a longer manufacturing time in the whole. In addition to this, there is the fact that each block must have a threading corresponding to that of the spindle part to be received and, accordingly, the blocks must be threaded oppositely.

A further drawback to be found especially with the use of this type of orthodontic screw, is related to the inevitable operational clearance of the screw connecting parts, so that the insufficient friction involved between the device's threaded parts in contact with each other may cause spontaneous rotations of the spindle, that is, a displacement of the blocks from their optimal position, especially when considering the strong reaction exerted by the members of the masticatory apparatus to which the prothesis elements are hooked up, and which has a natural tendency to displace the same prothesis from its proper operational position.

SUMMARY AND OBJECTS OF THE INVENTION

The main object of the present invention is to overcome the said drawbacks.

This result has been achieved, according to the invention, by adopting the idea of making an orthodontic expansion screw having a spindle with an end having a threaded portion. A block defines a through hole with an internal diameter larger than an external diameter of the threaded portion of the spindle. The threaded portion of the spindle is positioned in the through hole. Guide means guides movement of the block with respect to the spindle. Resin is cast inside the through hole and around the threaded portion to have the resin form a solid with a shape complementary to the threaded portion and to form a female thread engaging with the threaded portion of the spindle. The resin is also cast around the block to form an orthodontic plate interlocked with the block.

The advantages deriving from the present invention lie essentially in that it is possible to significantly reduce the manufacturing cost and time of this type of orthodontic screw and, at the same time, improve its working reliability and duration under any operating condition, inasmuch as some typical steps for the manufacturing of the conventional screws, such as the machining of the threaded bores within the blocks which receive the threaded parts of the spindle and the subsequent screw connection of these parts prior to the insertion thereof into the prothesis, result fully eliminated, so that it is no longer necessary to differentiate the construction of the blocks and, besides, the friction between the threaded parts results significantly increased, which allows the highest stability to be achieved regardless of the extent with which the two parts of the orthodontic plate or prothesis are spread apart.

These and other advantages and characteristics of the invention will be best understood by anyone skilled in the art from a reading of the following description in conjunction with the attached drawings given as a practical exemplification of the invention, but not to be considered in a limitative sense.

BRIEF DESCRIPTION OF THE DRAWINGS

FIG. 1A shows in detail a spindle with counter-rotating threads on the two sides, for an expansion screw of bidirectiona type;

FIG. 1B shows a sectional view taken on line IB—IB if FIG. 1A;

FIG. 1C shows the detail of two rods of the guide assembly in an expansion screw according to the invention;

DESCRIPTION OF THE PREFERRED EMBODIMENT

Figure 1D:
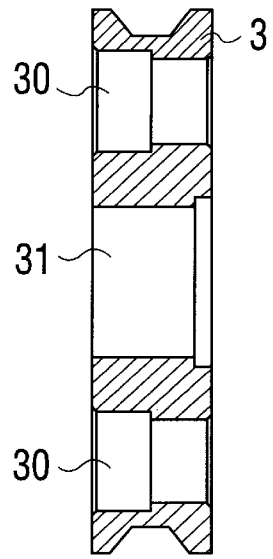
FIG. 1D shows the detail of a block of the guide assembly in an expansion screw according to the invention.
Figure 1E:
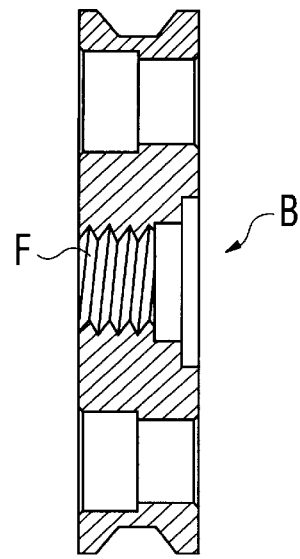
FIG. 1E shows the detail of the block of the guide assembly in a traditional expansion screw.
Figure 2A:
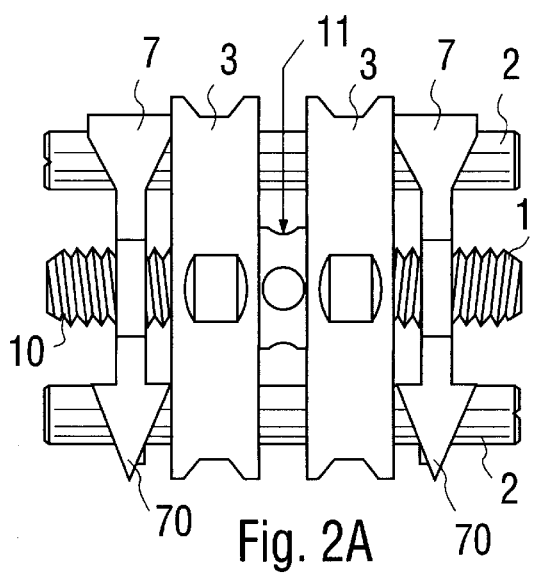
FIG. 2A shows the plan view of an orthodontic expansion screw according to the invention.
Figure 2B:
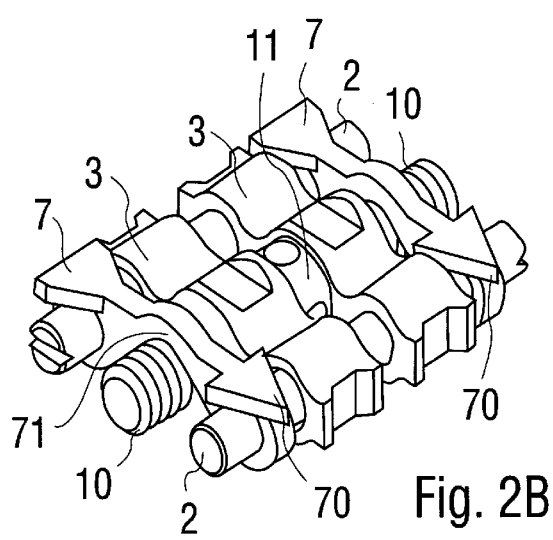
FIG. 2B shows a perspective view of the screw of FIG. 2A.
Figure 3A:
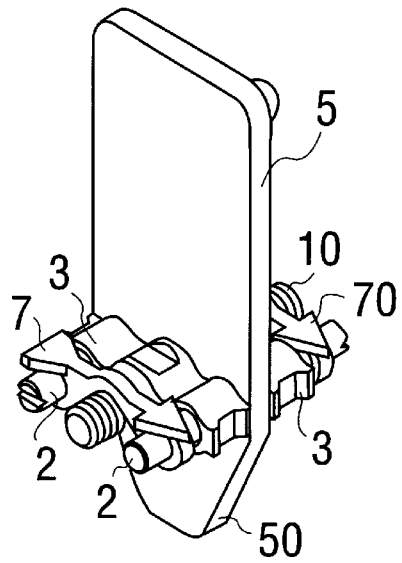
FIG. 3A shows a perspective view of an orthodontic expansion screw according to the invention, with a lamina which acts both as a seal and holding means for the positioning of the screw upon the application of a prothesis.
Figure 3B:
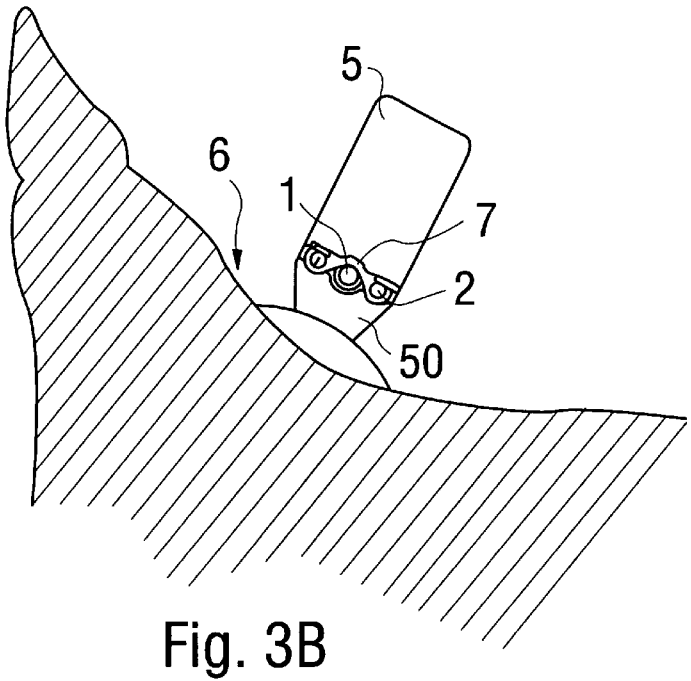
FIG. 3B shows a side view of the assembly of FIG. 3A in its operating position.
Figure 3C:
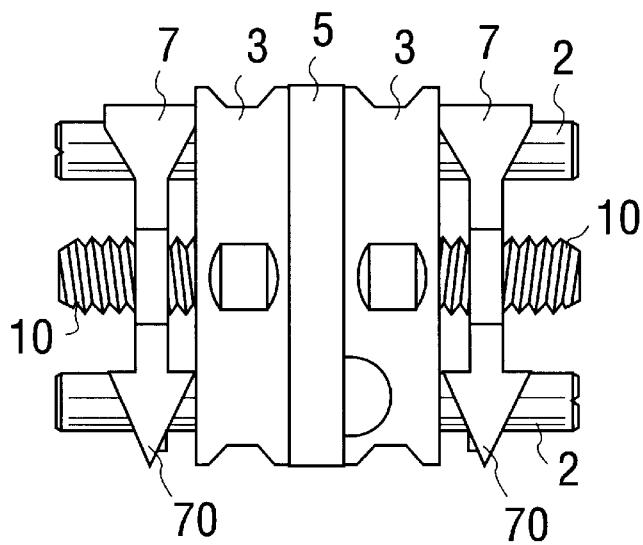
FIG. 3C shows a plan view of the assembly of FIG. 3A.

Reduced to its basic structure, and reference being made to FIGS. 1A–4B of the attached drawings, an orthodontic expansion screw according to the invention comprises a spindle (1) with counter-rotating threads on its two sides (10) and with a central enlargement (11) having a plurality of recesses or holes (12) to be individually engaged, by means of an actuating pin-like tool—not shown—with to drive spindle into rotation about its longitudinal axis (w—w). Associated with the spindle (1) are two cylindrical and parallel rods (2). These rods—which go through peripheral holes (30) of two blocks (3) located on opposite sides with respect to the enlargement (11) of spindle (1)—make up a slide guide for the movement of the two elements (40, 41) of the orthodontic plate (4), said elements (40, 41) being made integral to blocks (3) so as to have the elements of plate (4) connected between them through the assembly (1, 2, 3) which consists of the spindle (1), rods (2) and blocks (3). The assembly (1, 2, 3), as defined above, can be associated with a lamina spacer (5) made of synthetic resin or other suitable material, so as to be easily removable after or during the formation of the prothesis, the lower part (50) of said lamina allowing to support the screw for the positioning thereof on the plaster cast (6). The preparation of the plaster cast is carried out according to a technique known per se to those skilled in the art. A further function performed by the lamina (5) will be described later on. The thickness of the lamina (5) corresponds substantially to that of the actuating enlargement (11) on the spindle (1) and to the minimum distance between the two elements (40, 41) of the orthodontic plate (4). Such distance corresponds to that serving to create the partition cut between the two elements of the prothesis after the formation of the latter according to known techniques which comprise taking impressions, casting moulds and polymerizing synthetic resins. The execution of said cut by means of a suitable tool, makes it possible to dispose of the lamina (5) as a support for the screw during the formation of the prothesis. Provision is also made, advantageously, for two holder bodies (7) made of plastic material and positioned on opposite sides of the enlargement (11) of spindle (1). The bodies exhibit holes in which the rods (2) go through and cooperate in keeping the rods (2)-connecting blocks (3) within their seats. The two parts of each body (7) with the rods (2)-receiving holes are joined together through an arcuate connecting portion (71) having its concavity facing downwards and a radius substantially equal to that of each shank (10) of the spindle (1). One end (70) of each body (7) may be of arrow shape to indicate the operator the direction of rotation of the spindle (1) for the spreading apart of the prothesis, that is, the moving away of elements (40, 41) from the actuating enlargement (11).

Advantageously, according to the invention, each of said blocks (3) is provided with a central hole (31) for the positioning of a corresponding threaded shank (10) of spindle (1) going therethrough: the inner diameter of the hole (31) of each block (3) being larger than the external diameter of the relevant shank (10) to allow the resin to be introduced into the space between the wall of hole (31) and the threaded surface of the portion of the shank (10) present therein upon the formation of the prothesis. The hole (31) of each block (3) allowing the respective threaded shank (10) of spindle (1) to go therethrough has no female threading, contrary to the case of conventional screws.

Figure 4A:
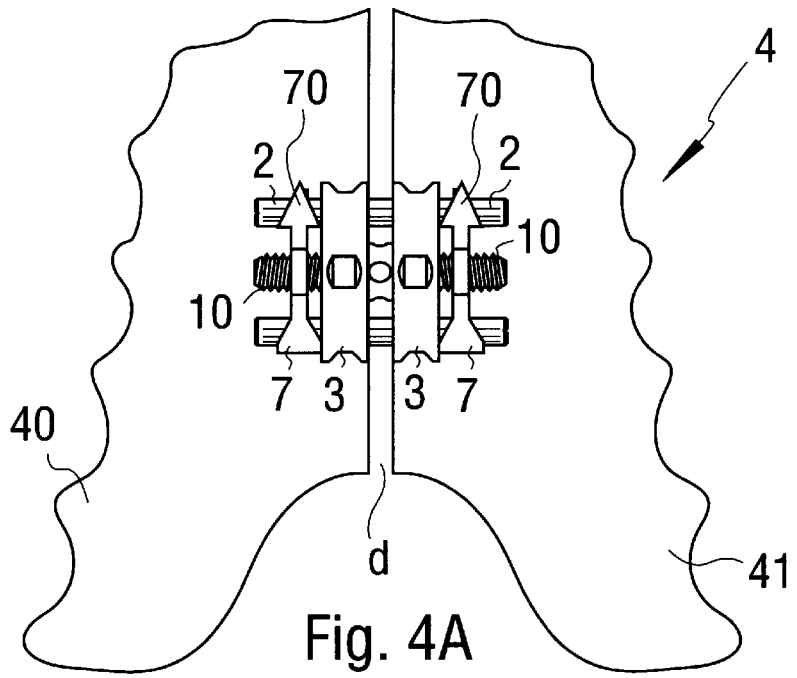
FIG. 4A shows a plan view of an orthodontic expansion screw according to the invention, associated with two parts of an orthodontic plate.
Figure 4B:
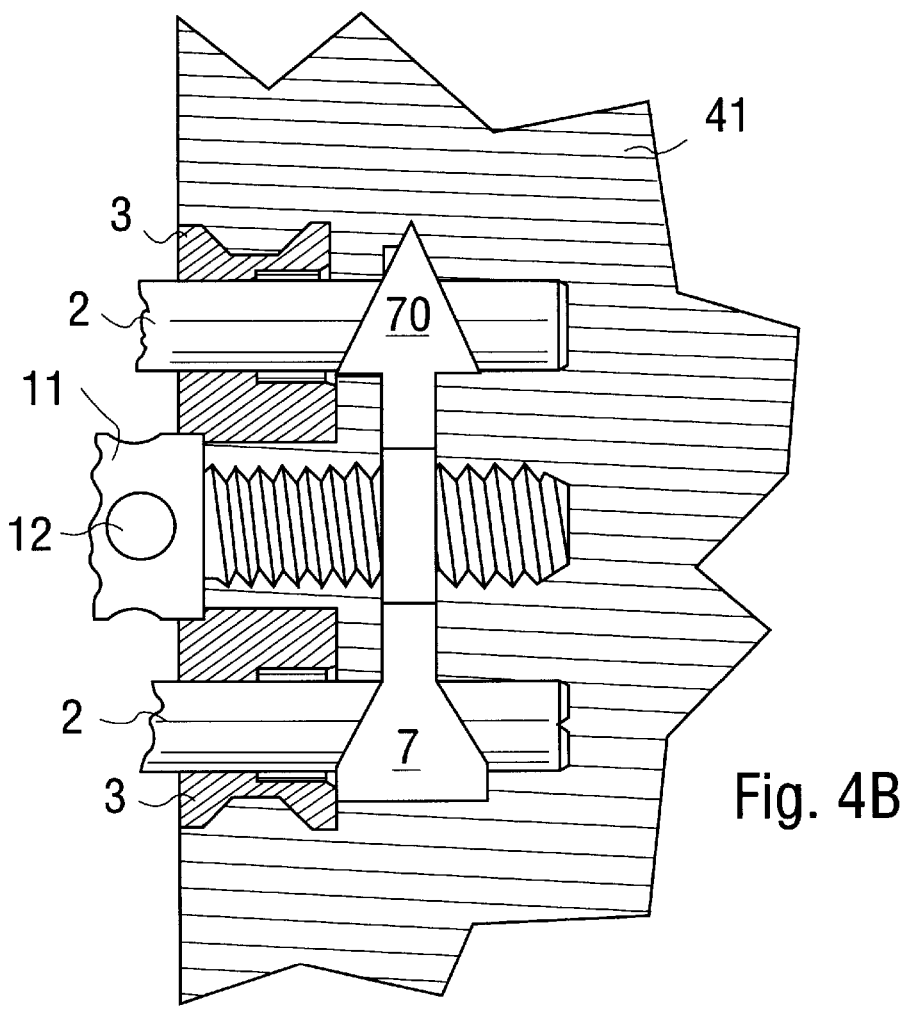
FIG. 4B shows an enlarged detail, partially in section, of the screw of FIG. 4A.

After positioning the screw within the resin of, for example, of acrylic type, for the formation of the orthodontic plate (4) which becomes interlocked with the block 3 as shown in FIG. 4B. The resin penetrates spontaneously the hole (31) of each block (3) and forms, in this way and with maximum precision and adhesion, the female threading on the respective shank (10) of spindle (1), so that, with the subsequent polimerization of the resin, each threaded shank (10) of spindle (1) will result already positioned within a corresponding body acting as a nut screw. Owing to the very close adhesion of the screw-nut screw coupling so accomplshed, and to the fact that such coupling involves the whole length of the shanks (10), that is, including the portions thereof protruding from the blocks (3), the maximum friction of the threads in contact with each other is thus obtained, while preventing the prothesis from self-closing when in use, that is, preventing blocks (3) from moving, together with the respective elements (40, 41) of plate (4), in a direction opposite to that imposed by the orthodentist. Moreover, any inaccuracy of tolerances in the threading on the shanks (10) of spindle (1) is also avoided, as the female screw takes shape spontaneously and directly on the threaded shanks of spindle (1).

In the course of the polimerization of the resin, that is, during the formation of the prothesis, the bodies (7), tight-fitted beforehand on the rods (2) and snap-fitted on the threaded surface of the respective shanks (10), ensure a steady adhesion of the blocks (3) on the walls of the lamina (5). The latter making up also a barrier against the infiltration of resin within the holes (12) of the actuating enlargement (11).

Figure 5A:
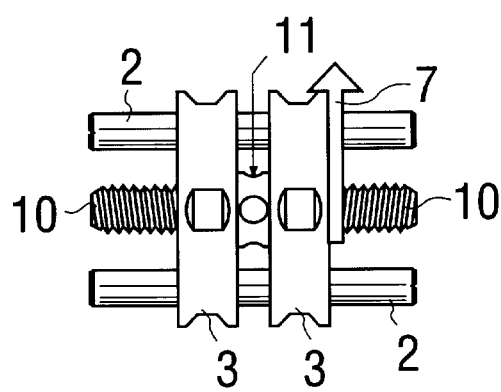
FIGS. 5A–5D show corresponding embodiments of an orthodontic expansion screws according to the invention.
Figure 5B:
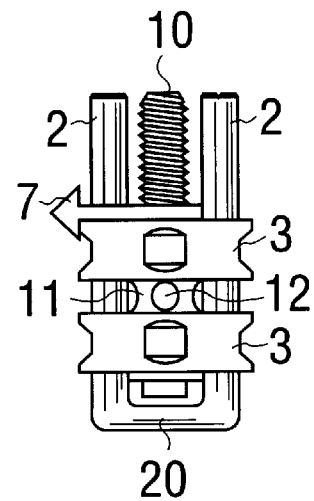
Figure 5C:
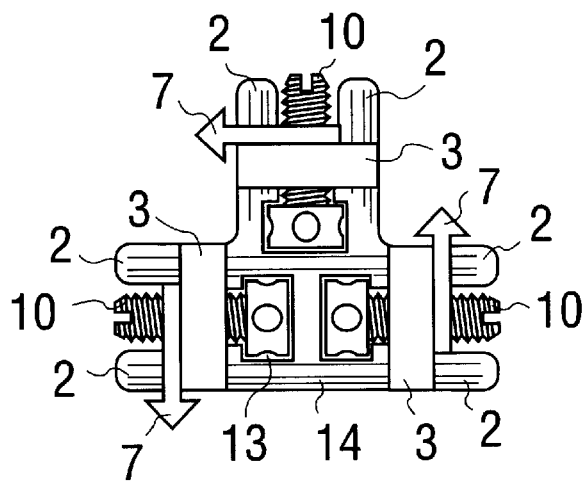
Figure 5D:
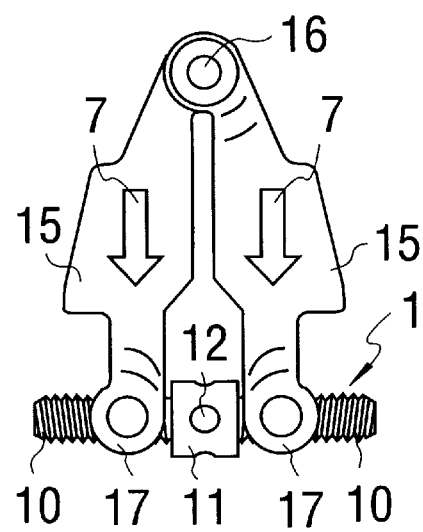

The invention may be applied both to bidirectional screws, as above described, and unidirectional, threedirectional and fan-like ones of the type illustrated in FIGS. 5A–5D of the attached drawings. More particularly, the screw of FIG. 5A is of bidirectional type, and the one of FIG. 5B is of unidirectional type, both having one guide-system rod (2) only and, in the case of FIG. 5B, a joining portion (20) is provided on the side opposite to that from which a single threaded shank (10) protrudes. The screw of FIG. 5C is of tridirectional type, with three independently operable spindles, each of which exhibits a respective threaded shank (10) going through a corresponding block (3), is associated with two parallel guide rods (2) and is inserted with its respective actuating head (11) into a seat (13) formed in a central supporting body (14). The screw of FIG. 5D is of a type so-called "with fan-like opening": connected with the spindle (1), which has an actuating head (11) centrally positioned, are two arms (15) hinged between them at a common point (16) a predetermined distance from the spindle (1). The front ends (17) of the arms (15) are provided with holes—not shown in the figure—allowing the threaded shanks (10) of spindle (1) to go therethrough and performing the same function as the blocks (3) previously described. By rotating the spindle (1) about its longitudinal axis, by means of the actuating head (11) being rotated in the direction of arrows (7), there is obtained the angular spreading apart of the arms (15).

A screw for orthodontic applications of this type is described in the patent application IT FI 95 A 175 to which reference is made for further details.

I claim:

1. An expansion orthodontic prothesis comprising:

a spindle with an end having a threaded portion;

a block defining a through hole with an internal diameter larger than an external diameter of said threaded portion of said spindle, said threaded portion of said spindle being positioned in said through hole;

guide means for guiding movement of said block with respect to said spindle;

resin cast inside said through hole and around said threaded portion to have said resin form a solid with a shape complementary to said threaded portion and to form a female thread engaging with said threaded portion of said spindle, said resin also cast around said block to form an orthodontic plate interlocked with said block.

2. The prothesis in accordance with claim 1, further comprising:

another block defining a through hole receiving another end of said spindle.

3. The prothesis in accordance with claim 2, further comprising:

another orthodontic plate formed by resin cast around said another block.

4. The prothesis in accordance with claim 3, wherein:

said another end of said spindle is opposite said end of said spindle, and said another end has a threaded portion counter rotating with respect to said threaded portion;

said through hole of said another block has an internal diameter larger than an external diameter of said threaded portion of said another end of said spindle;

said resin of said another orthodontic plate is also cast inside said through hole of said another block and around said threaded portion of said another end to have said resin form a solid with a shape complementary to said threaded portion of said another end and form a female thread engaging with said threaded portion of said another end of said spindle.

5. The prothesis in accordance with claim 2, wherein:

said guide means includes two substantially parallel rods positioned in peripheral holes of said block and said another block.

6. The prothesis in accordance with claim 2, wherein:

said guide means includes a hinge with two arms connected to said block and said another block.

7. The prothesis in accordance with claim 1, wherein:

said through hole is smooth and unthreaded.

8. The prothesis in accordance with claim 1, wherein:

said through hole has a circular cross section.

9. The prothesis in accordance with claim 1, wherein:

an actuating portion is provided on said spindle for rotating said spindle.

10. A method for forming an expansion orthodontic prothesis, the method comprising:

providing a spindle with an end having a threaded portion;

providing a block defining a through hole with an internal diameter larger than an external diameter of said threaded portion of said spindle, said threaded portion of said spindle being positioned in said through hole;

casting resin inside said through hole and around said threaded portion to have said resin form a solid with a shape complementary to said threaded portion and forming an engaging thread with said threaded portion, said resin also being cast around said block to form an orthodontic plate interlocked with said block.

11. The method in accordance with claim 10, further comprising providing an actuating portion on said spindle for rotating said spindle;

providing a spacer around said actuating portion before said casting;

providing a holder on said threaded portion and against said block to press said block against said spacer and prevent said resin from contacting said actuating portion during said casting.

12. An expansion orthodontic prothesis formed by the steps of:

providing a spindle with an end having a threaded portion;

providing a block defining a through hole with an internal diameter larger than an external diameter of said threaded portion of said spindle, said threaded portion of said spindle being positioned in said through hole;

casting resin inside said through hole and around said threaded portion to have said resin form a solid with a shape complementary to said threaded portion and forming an engaging thread with said threaded portion, said resin also being cast around said block to form an orthodontic plate interlocked with said block.

* * * * *